(12) United States Patent
Takahashi et al.

(10) Patent No.: US 10,736,610 B2
(45) Date of Patent: Aug. 11, 2020

(54) ULTRASONIC DIAGNOSTIC APPARATUS, ULTRASONIC DIAGNOSTIC APPARATUS CONTROL METHOD, AND MEDICAL IMAGE DIAGNOSTIC APPARATUS

(71) Applicant: Canon Medical Systems Corporation, Otawara-shi (JP)

(72) Inventors: Masami Takahashi, Nasushiobara (JP); Masamichi Oyanagi, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 950 days.

(21) Appl. No.: 14/192,237

(22) Filed: Feb. 27, 2014

(65) Prior Publication Data

US 2014/0180106 A1    Jun. 26, 2014

Related U.S. Application Data

(63) Continuation of application No. PCT/JP2012/072249, filed on Aug. 31, 2012.

(30) Foreign Application Priority Data

Aug. 31, 2011 (JP) .................................. 2011-190142
Aug. 31, 2012 (JP) .................................. 2012-191624

(51) Int. Cl.
*A61B 8/00* (2006.01)
*A61B 8/14* (2006.01)

(52) U.S. Cl.
CPC .................. *A61B 8/54* (2013.01); *A61B 8/14* (2013.01); *A61B 8/461* (2013.01); *A61B 8/467* (2013.01); *A61B 8/585* (2013.01); *A61B 8/469* (2013.01)

(58) Field of Classification Search
CPC .. A61B 8/14; A61B 8/54; A61B 8/461; A61B 8/467; A61B 8/469; A61B 8/585
See application file for complete search history.

(56) References Cited

U.S. PATENT DOCUMENTS 5,315,999 A  *  5/1994  Kinicki .................. A61B 8/467
                                                600/443
2007/0093713 A1 *  4/2007  Byron ...................... A61B 8/12
                                                600/437

(Continued)

FOREIGN PATENT DOCUMENTS

CN          1788687 A      6/2006
CN        101283916 A     10/2008

(Continued)

OTHER PUBLICATIONS

Chinese Office Action dated Jun. 4, 2014, in China Patent Application No. 201280001247.4 (with English Translation).

(Continued)

*Primary Examiner* — Jeffrey G Hoekstra
*Assistant Examiner* — Jason M Ip
(74) *Attorney, Agent, or Firm* — Oblon, McClelland, Maier & Neustadt, L.L.P.

(57) ABSTRACT

Various types of sub-preset conditions corresponding to a selected mother preset condition are read out from a preset condition storage unit which stores at least a plurality of mother preset conditions set concerning image data acquisition conditions and various types of sub-preset conditions set by updating all or some of the image data acquisition conditions included in each of the mother preset conditions. A sub-preset condition suitable for ultrasonic examination on the object is selected from the readout various types of sub-preset conditions. An image data acquisition condition is initialized based on the selected mother preset condition with respect to each unit related to generation of the image (Continued)

data. The image data acquisition condition is updated by using the selected sub-preset condition. Image data is generated based on a reception signal in ultrasonic transmission/reception using the updated image data acquisition condition.

26 Claims, 13 Drawing Sheets

(56) References Cited

U.S. PATENT DOCUMENTS

| | | | |
|---|---|---|---|
| 2008/0146929 A1 | 6/2008 | Satoh | |
| 2008/0161688 A1* | 7/2008 | Poland | A61B 8/00 600/437 |
| 2008/0269610 A1* | 10/2008 | Burla | A61B 8/00 600/447 |

FOREIGN PATENT DOCUMENTS

| | | |
|---|---|---|
| JP | 2002-113006 A | 4/2002 |
| JP | 2007-111439 A | 5/2007 |
| JP | 2010-029351 A | 2/2010 |
| JP | 2010-240198 A | 10/2010 |
| WO | WO 2010/055820 A1 | 5/2010 |

OTHER PUBLICATIONS

International Preliminary Report on Patentability and Written Opinion dated Mar. 13, 2014 in Application No. PCT/JP2012/072249.
International Search Report dated Nov. 20, 2012 for PCT/JP2012/072249 filed Aug. 31, 2012 with English Translation.
International Written Opinion dated Nov. 20, 2012 for PCT/JP2012/072249 filed Aug. 31, 2012.

* cited by examiner

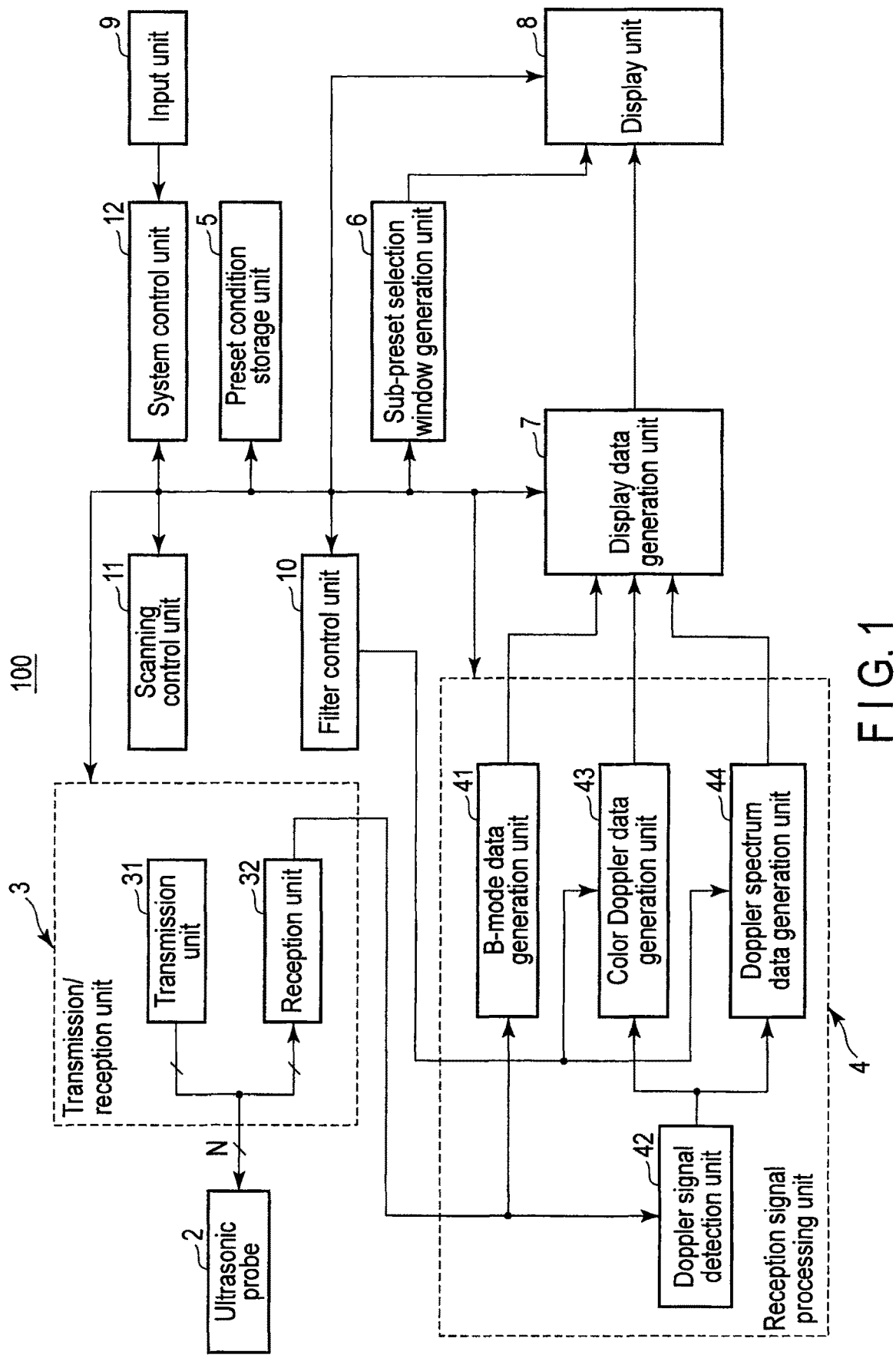
F I G. 1

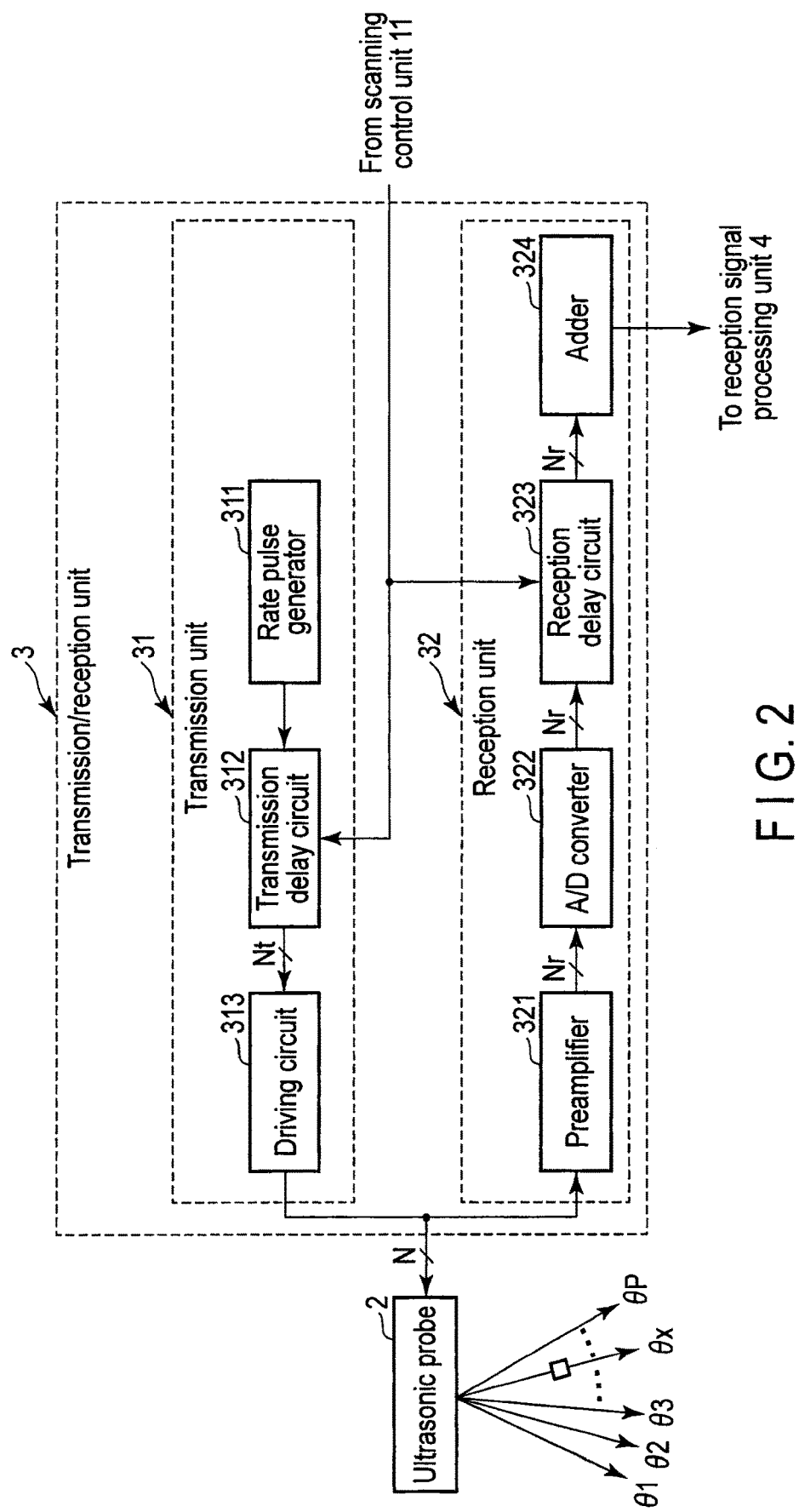
F I G. 2

Mother preset condition MPa

| Imaging mode | Mother preset item | Mother preset condition |
|---|---|---|
| B mode | Observation depth (D) | Dx(mm) |
| | Ultrasonic wave focusing distance (F) | Fx(mm) |
| | Scanning range (W) | Wx(deg, mm) |
| | Ultrasonic frequency (fo) | fox(Hz) |
| | Reception gain (G) | Gx(dB) |
| Color Doppler mode | Rate frequency (fr) | frx(Hz) |
| | Filter frequency (fc) | fcx(Hz) |
| | Ultrasonic frequency (fo) | fox(Hz) |
| | Reception gain (G) | Gx(dB) |
| Spectrum Doppler mode | Rate frequency (fr) | frx(Hz) |
| | Filter frequency (fc) | fcx(Hz) |
| | Ultrasonic frequency (fo) | fox(Hz) |
| | Reception gain (G) | Gx(dB) |
| | Baseline shift frequency (fs) | fsx(Hz) |

FIG. 5

| Sub-preset condition | | |
|---|---|---|
| Sub-preset name | Sub-preset item | Sub-preset condition |
| Ba1 | Observation depth (D) | Da1(mm) |
| | Ultrasonic wave focusing distance (F) | Fa1(mm) |
| | Scanning range (W) | Wa1(deg) |
| Ba2 | Observation depth (D) | Da2(mm) |
| | Scanning range (W) | Wa2(deg) |
| | Reception gain (G) | Ga2(dB) |
| Ba3 | Observation depth (D) | Da3(mm) |
| | Scanning range (W) | Wa3(deg) |
| Ba4 | Observation depth (D) | Da4(mm) |

F I G. 6

Sub-preset condition

| Sub-preset name | Sub-preset item | Sub-preset condition |
|---|---|---|
| Ba1 | Observation depth (D) | Da1(mm) |
| | Ultrasonic wave focusing distance (F) | Fa1(mm) |
| | Scanning range (W) | Wa1(deg) |
| Ba2 | Observation depth (D) | Da2(mm) |
| | Ultrasonic wave focusing distance (F) | Fa2(mm) |
| | Scanning range (W) | Wa2(deg) |
| Ba3 | Observation depth (D) | Da3(mm) |
| | Scanning range (W) | Wa3(deg) |
| …… | …… | …… |

F I G. 7

| Sub-preset condition | | |
|---|---|---|
| Sub-preset name | Sub-preset item | Sub-preset condition |
| Ba1 | Observation depth (D) | Da1(mm) |
| | Ultrasonic wave focusing distance (F) | Fa1(mm) |
| | Scanning range (W) | Wa1(deg) |
| ...... | ...... | ...... |
| Ba9 | Application | Ap2 |
| Ba10 | Probe type | 6C3 |
| Ba11 | Ultrasonic wave focusing distance (F) | Fa10(mm) |

F I G. 8

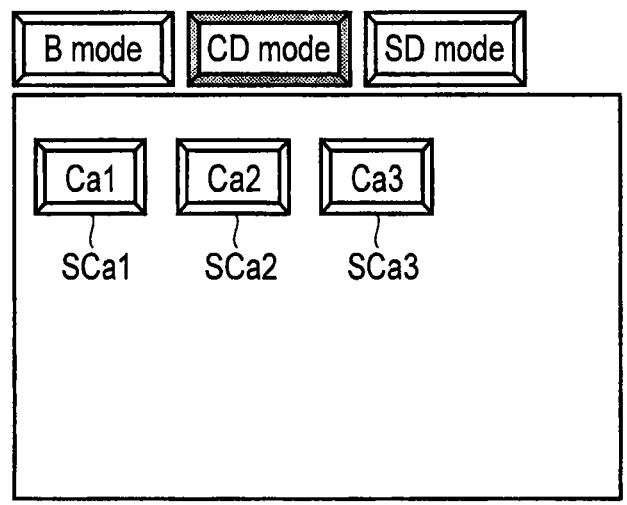
F I G. 9C
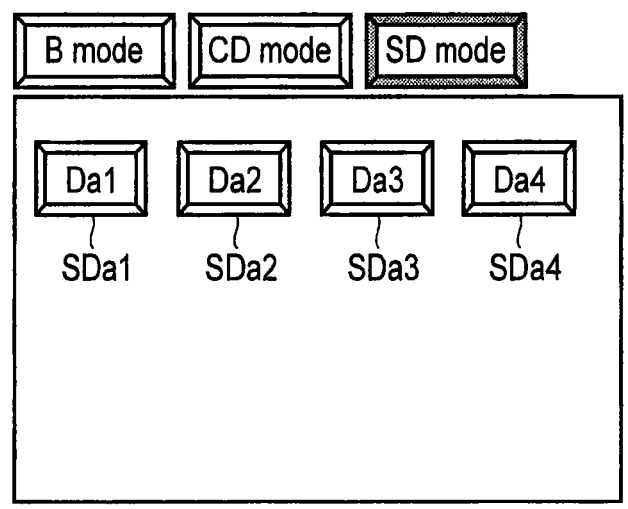
F I G. 9D

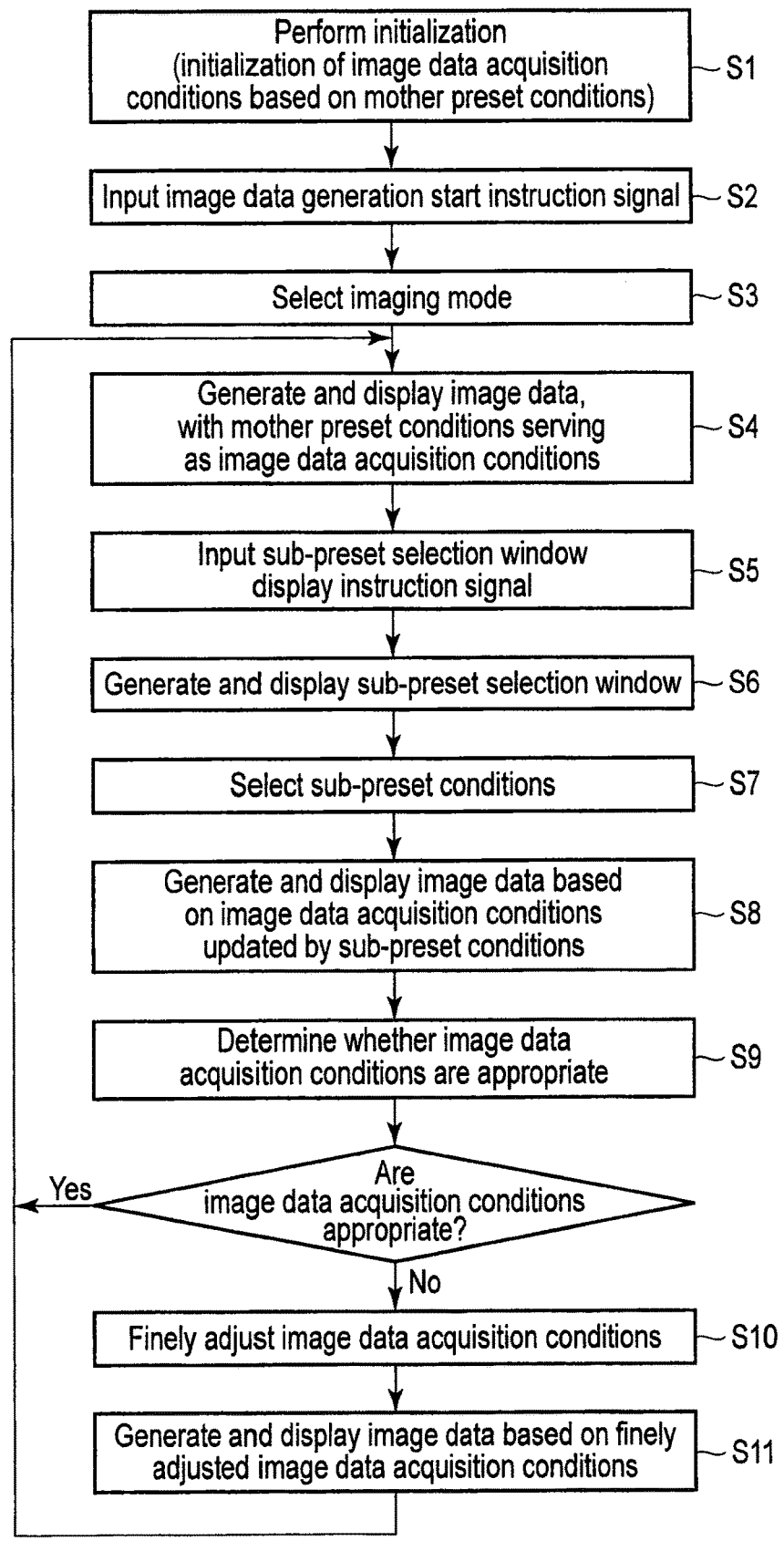
F I G. 11

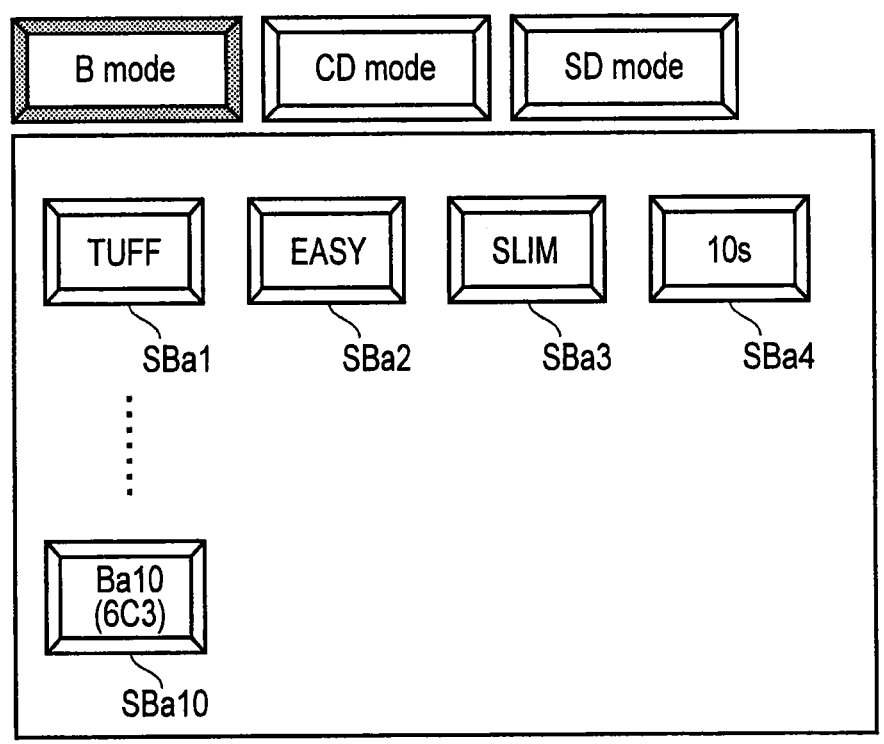
F I G. 12

ULTRASONIC DIAGNOSTIC APPARATUS, ULTRASONIC DIAGNOSTIC APPARATUS CONTROL METHOD, AND MEDICAL IMAGE DIAGNOSTIC APPARATUS

CROSS-REFERENCE TO RELATED APPLICATION

This application is a Continuation Application of PCT Application NO. PCT/JP2012/072249, based upon and claims the benefit of priority from Japanese Patent Application No. 2011-190142, filed Aug. 31, 2011, and the Japanese Patent Application No. 2012-191624, filed Aug. 31, 2012, the entire contents of which are incorporated herein by reference.

FIELD

Embodiments described herein relate generally to an ultrasonic diagnostic apparatus which transmits and receives ultrasonic waves to and from an object based on preset conditions set in advance, an ultrasonic diagnostic apparatus control method, and a medical image diagnostic apparatus.

BACKGROUND

An ultrasonic diagnostic apparatus is designed to apply ultrasonic pulses generated by transducers incorporated in an ultrasonic probe into an object to be examined, convert reflected waves generated by the difference in acoustic impedance between object tissues into electrical signals through the transducers, and display the resultant image on a monitor. This diagnostic method allows easy acquisition of various types of image data by simple operation of only bringing the ultrasonic probe into contact with the body surface, and hence is widely used for functional diagnosis or morphological diagnosis of various organs.

Ultrasonic diagnostic methods of obtaining biological information by using reflected waves from tissues or blood cells in a living body have rapidly progressed along with two great technical developments of an ultrasonic pulse reflection method and ultrasonic Doppler method. B-mode image data and color Doppler image data obtained by these techniques have become indispensable to recent ultrasonic diagnosis. In addition, a spectrum Doppler method for acquiring spectrum image data that allows quantitative measurement of blood flow information of a diagnostic target region is used for circulatory organ regions, abdominal regions, and the like.

When performing ultrasonic examination on an object by sequentially acquiring these image data, although image data acquisition conditions constituted by many imaging parameters suitable for the acquisition of the respective image data are set before examination, it is necessary to set the respective imaging parameters used for ultrasonic examination for each examination based on not only the imaging modes set when acquiring the above image data (i.e., the B mode, color Doppler mode, and spectrum Doppler mode) but also the body type, age, and the like of the object. For this reason, it takes much time to set image data acquisition conditions optimal for such ultrasonic examination, leading to a deterioration in examination efficiency.

In order to solve such a problem, there has recently been practiced a method of initializing a preset standard image data acquisition condition as a preset condition (to be described later as a mother preset condition) and acquiring desired image data by finely adjusting the preset condition under the observation of image data acquired based on the preset condition.

Setting the above preset condition before ultrasonic examination makes it possible to efficiently set image data acquisition conditions. However, as has been described above, since optimal image data acquisition conditions vary depending on the body type, age, and the like of the object, it is often necessary to change and update some of the initialized preset conditions during the examination.

In such a case, the above conventional method has a problem that, for example, since the image data acquisition conditions newly set by updating the preset conditions in the preceding imaging mode return to the image data acquisition conditions in the initialized imaging mode when the imaging mode shifts to the subsequent imaging mode, it is necessary to reset each preset condition every time an imaging mode is restarted or a new imaging mode is selected.

This disclosure has been made in consideration of the above problem. It is an object to provide an ultrasonic diagnostic apparatus which updates image data acquisition conditions initialized by using a mother preset condition set in advance, based on sub-preset conditions set for each imaging mode as a unit, and can acquire desired image data in a short period of time by generating image data based on the image data acquisition conditions after the update, an ultrasonic diagnostic apparatus control method, and a medical image diagnostic apparatus.

BRIEF DESCRIPTION OF DRAWINGS

FIG. 1 is a block diagram showing the overall arrangement of an ultrasonic diagnostic apparatus according to this embodiment.

FIG. 2 is a block diagram showing the concrete arrangement of the transmission/reception unit of the ultrasonic diagnostic apparatus according to this embodiment.

FIG. 5 is a view showing a concrete example of mother preset conditions in this embodiment.

FIG. 6 is a view showing a concrete example of sub-preset conditions in this embodiment.

FIG. 7 is a view showing a modification of sub-preset conditions in this embodiment.

FIG. 8 is a view showing a modification of sub-preset conditions in this embodiment.

FIG. 9C is a view showing a concrete example of a sub-preset selection window in this embodiment.

FIG. 9D is a view showing a concrete example of a sub-preset selection window in this embodiment.

FIG. 11 is a flowchart showing a setting/updating procedure for image data acquisition conditions in this embodiment.

FIG. 12 is a view showing a modification of the sub-preset selection window in this embodiment.

DETAILED DESCRIPTION

Figure 3:
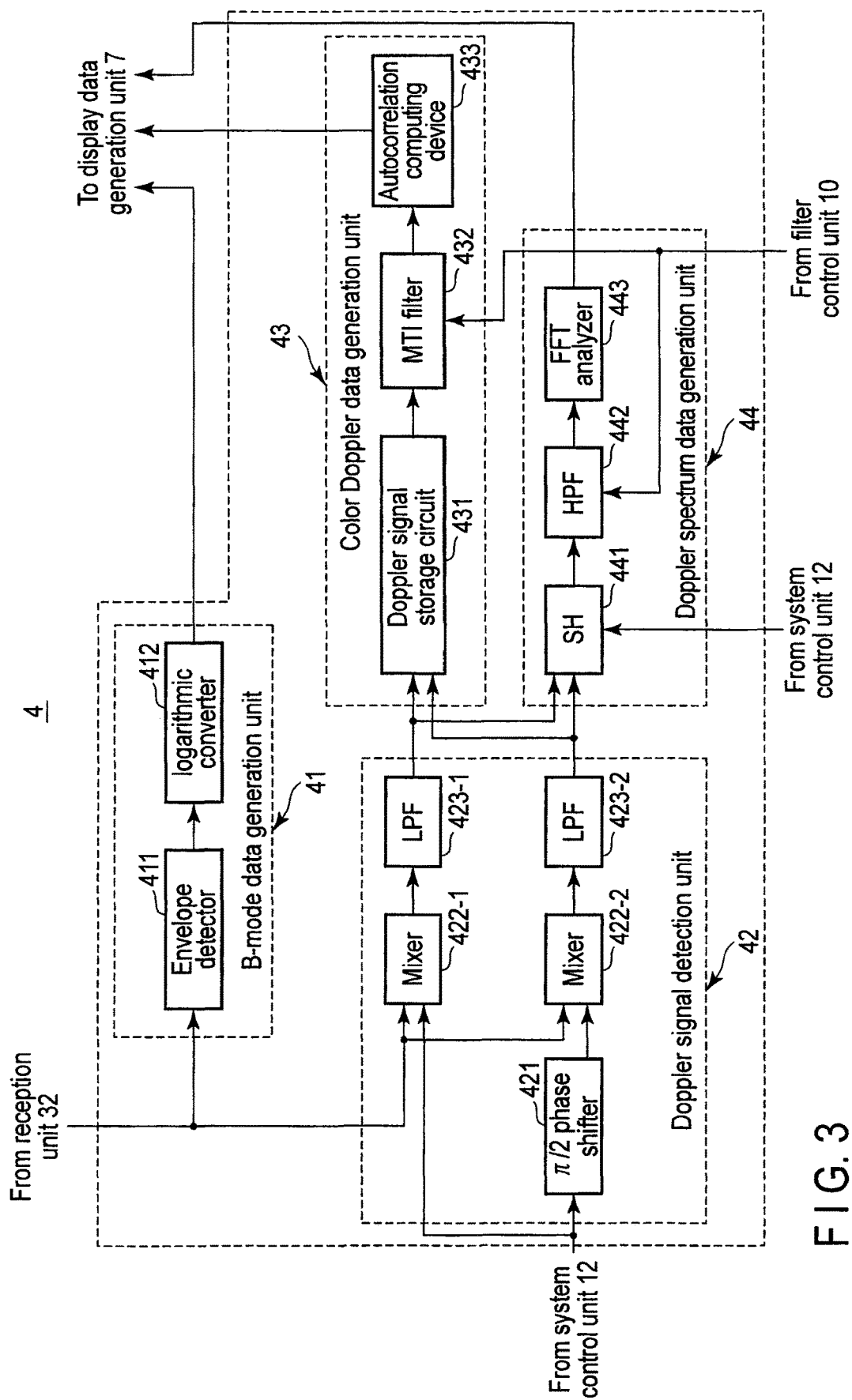
FIG. 3 is a block diagram showing the concrete arrangement of the reception signal processing unit of the ultrasonic diagnostic apparatus of this embodiment.

An ultrasonic diagnostic apparatus disclosed by this embodiment comprises a preset condition storage which stores a plurality of mother preset conditions and various types of sub-preset conditions, the mother preset conditions being concerned with at least image data acquisition conditions and the sub-preset conditions being set by updating all or some of the image data acquisition conditions included in each of the mother preset conditions; a sub-preset condition selection unit configured to read out the various types of sub-preset conditions corresponding to a selected mother preset condition from the preset condition storage unit and select a sub-preset condition suitable for ultrasonic examination on the object from the readout various types of sub-preset conditions; an acquisition condition control unit configured to initialize an image data acquisition condition based on the selected mother preset condition with respect to each unit related to generation of the image data and update the image data acquisition condition by using the selected sub-preset condition; and an image data generation unit configured to generate image data based on a reception signal in ultrasonic transmission/reception using the updated image data acquisition condition.

An embodiment of this disclosure will be described below with reference to the accompanying drawing.

Embodiment

According to the ultrasonic diagnostic apparatus of this embodiment to be described below, image data acquisition conditions are initialized by using conditions or values (to be referred to as "mother preset conditions" hereinafter or to be also referred to as "user presets" or "imaging presets" hereinafter) concerning a plurality of parameters set in the ultrasonic diagnostic apparatus which are preset for each ultrasonic examination as a unit. This ultrasonic diagnostic apparatus then updates (changes or adjusts) a condition concerning at least one parameter included in image data acquisition conditions initialized based on mother preset conditions by using a condition or value (sub-preset condition) concerning at least one parameter set in the apparatus for each imaging mode as a unit, and generates image data based on the image data acquisition conditions after the update. The operator then observes the image data obtained as the result of this operation to determine whether the image data acquisition conditions after the update are appropriate. If they are not appropriate, the operator finely adjusts the image data acquisition conditions by using input devices of an input unit.

This embodiment will exemplify an ultrasonic diagnostic apparatus which can acquire B-mode image data, color Doppler image data, and spectrum image data. However, the embodiment is not limited to this and may be an ultrasonic diagnostic apparatus which can acquire B-mode image data and color Doppler image data or B-mode image data and spectrum image data or an ultrasonic diagnostic apparatus which can acquire any one of the following data: B-mode image data, color Doppler image, and spectrum image data.

Although the following description will exemplify an ultrasonic diagnostic apparatus which generates the above image data based on the reception signals obtained by sector scanning on an object, this embodiment may be an ultrasonic diagnostic apparatus which can perform other types of ultrasonic scanning such as convex scanning and linear scanning.

This embodiment will also exemplify a parameter setting/updating method using mother preset conditions and sub-preset conditions using, for example, an ultrasonic diagnostic apparatus. However, the application of the parameter setting/updating method is not limited to an ultrasonic diagnostic apparatus. For example, this method can be applied to parameter setting/updating operation in various types of medical image diagnostic apparatuses typified by an X-ray diagnostic apparatus, X-ray computed tomography apparatus, magnetic resonance imaging apparatus, and nuclear medicine diagnostic apparatus.

(Apparatus Arrangement)

The arrangement and function of the ultrasonic diagnostic apparatus according to the embodiment in this disclosure will be described with reference to FIGS. 1, 2, 3, 4, 5, 6, 7, and 8. Note that FIG. 1 is a block diagram showing the overall arrangement of the ultrasonic diagnostic apparatus according to this embodiment, and FIGS. 2, 3, and 8 are block diagrams showing the concrete arrangements of the transmission/reception unit, reception signal processing unit, and display data generation unit of this ultrasonic diagnostic apparatus.

An ultrasonic diagnostic apparatus 100 shown in FIG. 1 includes an ultrasonic probe 2, a transmission/reception unit 3, a reception signal processing unit 4, a preset condition storage unit 5, a sub-preset selection window generation unit 6, a display data generation unit 7, a display unit 8, an input unit 9, a filter control unit 10, a scanning control unit 11, and a system control unit 12.

The ultrasonic probe 2 includes an array of a plurality of transducers which emit ultrasonic pulses (transmission ultrasonic waves) into the body of an object and convert the reflected ultrasonic waves (reception ultrasonic waves) obtained from the inside of the body by the transmission ultrasonic waves into electrical signals (reception signals). The transmission/reception unit 3 supplies driving signals for applying transmission ultrasonic waves in a predetermined direction in the object to the transducers, and performs phased addition of reception signals through a plurality of channels which are obtained from the transducers. The reception signal processing unit 4 generates B-mode data, color Doppler data, and Doppler spectrum data by processing the reception signals after phased addition which are obtained in the B mode, color Doppler mode (CD mode), and spectrum Doppler mode (SD mode). The preset condition storage unit 5 stores mother preset conditions set in advance for each ultrasonic examination as a unit and sub-preset conditions set in advance for each imaging mode as a unit. The sub-preset selection window generation unit 6 generates sub-preset selection window data in a predetermined format based on the sub-preset conditions read out from the preset condition storage unit 5. The display data generation unit 7 generates various types of image data based on the B-mode data, color Doppler data, and Doppler spectrum data generated by the reception signal processing unit 4, and generates display data based on the image data. The display unit 8 displays the above display data generated by the display data generation unit 7 and the sub-preset selection window data supplied from the sub-preset selection window generation unit 6. The input unit 9 is a device by which, for example, the operator inputs object information, selects an imaging mode, selects sub-preset conditions, and inputs various types of instruction signals. The filter control unit 10 controls the filtering characteristics of the MTI (Moving Target Indication) filter and HPF (High-Pass Filter) of the reception signal processing unit 4 based on the mother preset conditions, sub-preset conditions, and the like supplied from the preset condition storage unit 5 via the system control unit 12. The scanning control unit 11 controls the ultrasonic transmission/reception direction and ultrasonic wave focusing distance relative to the object based on the above mother preset conditions, sub-preset conditions, and the like. The system control unit 12 comprehensively controls the respective units described above. The arrangement and function of each unit will be described in detail below.

The ultrasonic probe 2 has an array of N transducers (not shown) at its distal end portion. The distal end is brought into contact with the body surface of an object to transmit/receive ultrasonic waves. The transducers are electroacoustic conversion elements each having a function of converting an electrical driving signal into a transmission ultrasonic wave at the time of transmission and converting a reception ultrasonic wave into an electrical reception signal at the time of reception. These transducers are connected to the transmission/reception unit 3 via an N-channel multicore cable. Although this embodiment will exemplify a case of using the ultrasonic probe 2 for sector scanning which includes N transducers, the embodiment may use an ultrasonic probe corresponding to linear scanning, convex scanning, or the like.

The transmission/reception unit 3 shown in FIG. 2 includes a transmission unit 31 which supplies, to the transducers of the ultrasonic probe 2, driving signals for emitting ultrasonic pulses in the respective types of imaging modes (i.e., the B mode, color Doppler mode, and spectrum Doppler mode) in a predetermined direction in an object, and a reception unit 32 which performs phased addition of reception signals in a plurality of channels which are obtained from these transducers. The transmission unit 31 includes a rate pulse generator 311, a transmission delay circuit 312, and a driving circuit 313.

The rate pulse generator 311 generates rate pulses for determining the repetition period of transmission ultrasonic waves emitted into the object, based on the mother preset conditions, sub-preset conditions, and the like supplied from the system control unit 12, and supplies the obtained rate pulses to the transmission delay circuit 312. Note that the above rate pulse repletion period is decided based on the observation depth or rate frequency of the mother preset conditions or sub-preset conditions to be described later.

The transmission delay circuit 312 is constituted by independent delay circuits equal in number to Nt transmission transducers selected from the N transducers incorporated in the ultrasonic probe 2. The transmission delay circuit 312 gives the above rate pulses output from the rate pulse generator 311 focusing delay times for focusing transmission ultrasonic waves to a predetermined depth to obtain a small beam width at the time of transmission and deflection delay times for emitting the transmission ultrasonic waves in a predetermined direction, in accordance with the scanning control signals supplied from the scanning control unit 11 based on the above mother preset conditions, sub-preset conditions, and the like.

The driving circuit 313 has a function of driving the Nt transmission transducers incorporated in the ultrasonic probe 2, and generates driving pulses having focusing delay times for focusing transmission ultrasonic waves to a predetermined depth (distance) and deflection delay times for emitting the ultrasonic waves in a predetermined direction based on the rate pulses supplied from the transmission delay circuit 312.

The reception unit 32 includes a preamplifier 321, A/D converter 322, reception delay circuit 323, and adder 324 in Nr channels corresponding to the Nr reception transducers selected from the N transducers incorporated in the ultrasonic probe 2. The A/D converter 322 converts reception signals in the Nr channels, which are supplied from the reception transducers via the preamplifier 321 in the B mode, color Doppler mode, and spectrum Doppler mode, into digital signals, and sends them to the reception delay circuit 323.

The reception delay circuit 323 gives the respective reception signals in the Nr channels, which are output from the A/D converter 322, focusing delay times for focusing reception ultrasonic waves from a predetermined depth and deflection delay times for setting strong reception directivity in a predetermined direction in accordance with the scanning control signals supplied from the scanning control unit 11 based on mother preset conditions, sub-preset conditions, and the like. The adder 324 adds and combines Nr-channel reception signals output from the reception delay circuit 323. That is, the reception delay circuit 323 and the adder 324 perform phased addition of reception signals corresponding to reception ultrasonic waves from a predetermined direction.

Note that the transmission delay circuit 312 and the reception delay circuit 323 decide focusing delay times and deflection delay times based on the ultrasonic wave focusing distance, scanning range, and the like of mother preset conditions or sub-preset conditions to be described later.

The reception signal processing unit 4 shown in FIG. 3 includes a B-mode data generation unit 41 which generates B-mode data by processing the B-mode reception signal output from the adder 324 of the reception unit 32, a Doppler signal detection unit 42 which detects the Doppler signal mixed in reception signals in the color Doppler mode and spectrum Doppler mode by performing quadrature detection of the reception signals, a color Doppler data generation unit 43 which generates color Doppler data based on the Doppler signal detected in the color Doppler mode, and a Doppler spectrum data generation unit 44 which generates Doppler spectrum data based on the Doppler signal detected in the spectrum Doppler mode.

The B-mode data generation unit 41 includes an envelope detector 411 and a logarithmic converter 412. The envelope detector 411 performs envelope detection of the reception signal after phased addition which is supplied from the adder 324 of the reception unit 32. The logarithmic converter 412 generates B-mode data by logarithmically converting the amplitude of the envelope-detected reception signal.

The Doppler signal detection unit 42 includes a $\pi/2$ phase shifter 421, mixers 422-1 and 422-2, and LPFs (Low-Pass Filters) 423-1 and 423-2, and detects a complex Doppler signal constituted by real and imaginary parts by performing quadrature detection of the reception signal supplied from the adder 324 of the reception unit 32.

The color Doppler data generation unit 43 includes a Doppler signal storage circuit 431, an MTI filter 432, and an autocorrelation computing device 433. The Doppler signal storage circuit 431 stores the complex components of the Doppler signals output from the LPFs 423-1 and 423-2 of the Doppler signal detection unit 42 at times of ultrasonic transmission/reception in the same direction, i.e., real components (I components) and imaginary components (Q components).

The MTI filter 432 serving as a digital filter for the removal of low-frequency components sequentially reads out time-series Doppler signals acquired from the same region in the object from the Doppler signal storage circuit 431. The MTI filter 432 then extracts components originating from blood flows (blood flow components) included in these Doppler signals, and removes components (clutter components) originating from the respiratory motion, pulsatory motion, and the like of an organ. More specifically, setting the cutoff frequency or the like of the MTI filter 432 to a suitable value will separate the above blood flow components and clutter components having lower frequencies than the blood flow components.

The autocorrelation computing device 433 calculates, as color Doppler data, an average flow velocity value of blood flows, a velocity variance indicating blood flow velocity fluctuations, a power value indicating the magnitude of a blood flow component, and the like by performing autocorrelation computation of the blood flow components of the Doppler signals extracted by the MTI filter 432.

The Doppler spectrum data generation unit 44 includes an SH (Sample Hold circuit) 441, an HPF (High-Pass Filter) 442, and an FFT (Fast-Fourier-Transform) analyzer 443, and generates Doppler spectrum data by frequency-analyzing the Doppler signal in the spectrum Doppler mode which is supplied from the Doppler signal detection unit 42.

The SH 441 receives the real and imaginary components of the Doppler signals output from the LPFs 423-1 and 423-2 of the Doppler signal detection unit 42 and the position information of a region of interest (range gate) set by the input unit 9. The SH 441 then extracts a Doppler signal corresponding to the region of interest from the Doppler signals acquired in a time-series manner by a plurality of times of ultrasonic transmission/reception in a predetermined direction. On the other hand, the HPF 442 removes clutter components originating from the respiratory motion, pulsatory motion, and the like of the organ which are included in this Doppler signal by filtering processing of the Doppler signal in the region of interest which is output from the SH 441.

The FFT analyzer 443 includes a computation circuit and storage circuit (not shown), and temporarily stores the Doppler signal of the region of interest which is output from the HPF 442 in the storage circuit. On the other hand, the computation circuit generates Doppler spectrum data by frequency-analyzing the Doppler signal in a predetermined period which is stored in the storage circuit.

Note that a filter order, cutoff frequency, and the like which decide the frequency characteristics of the MTI filter 432 of the color Doppler data generation unit 43 and the HPF 442 of the Doppler spectrum data generation unit 44 are decided based on the filter frequency and the like of mother preset conditions or sub-preset conditions to be described later. The baseline of the Doppler spectrum data generated by the FFT analyzer 443 is decided based on a baseline shift frequency and the like.

The preset condition storage unit 5 shown in FIG. 1 includes a mother preset condition storage unit and sub-preset condition storage unit (not shown). Each storage unit stores mother preset conditions set in advance for each ultrasonic examination as a unit and sub-preset conditions set in advance for each imaging board as a unit.

Figure 4:
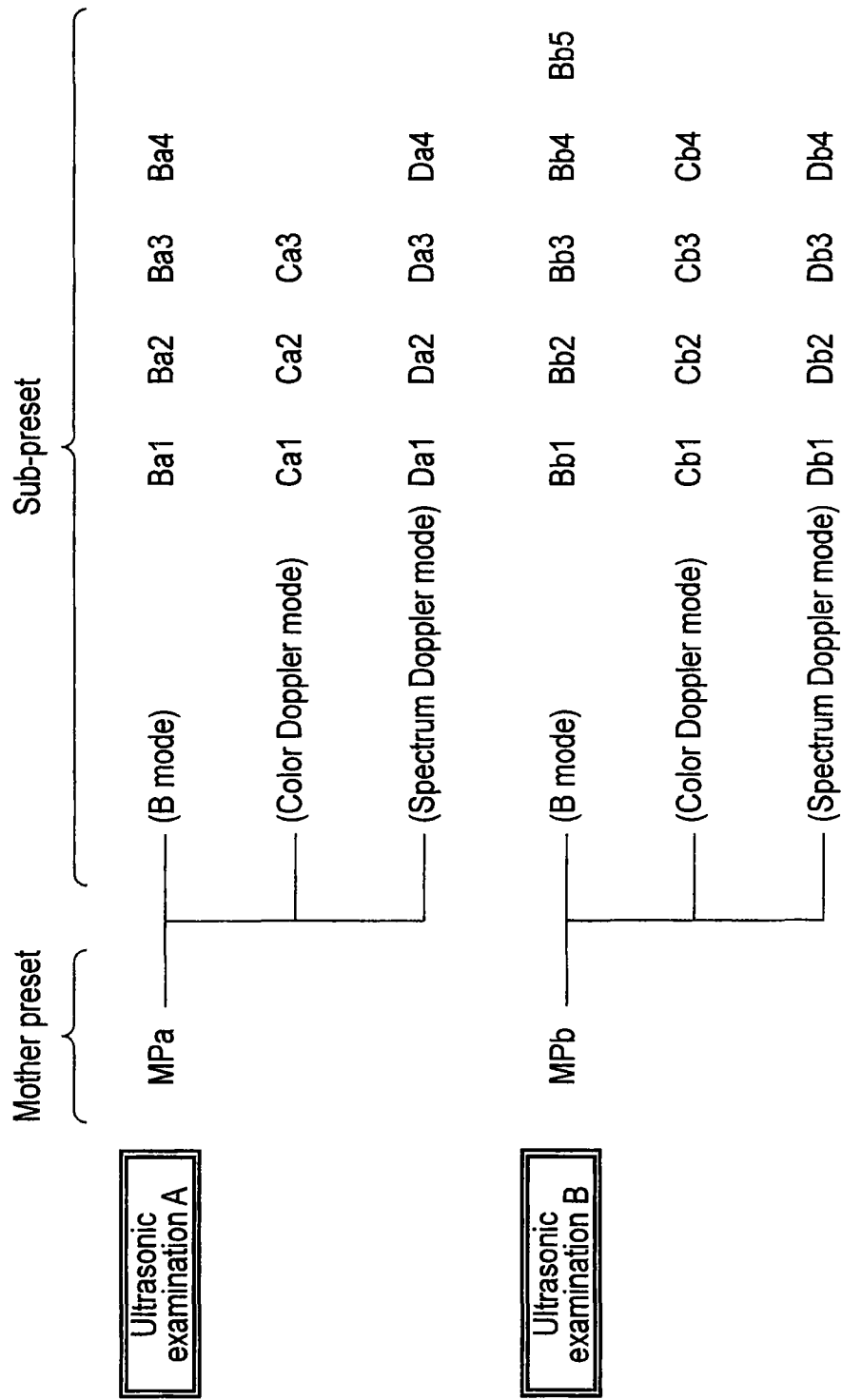
FIG. 4 is a view for explaining mother presets and sub-presets in this embodiment.

FIG. 4 shows the relationship between mother preset conditions and sub-preset conditions. This embodiment performs presetting operation of setting/updating image data acquisition conditions using mother preset conditions and sub-preset conditions by combining the mother preset conditions initialized for each ultrasonic examination as a unit and a plurality of sub-preset conditions used to update some of the mother preset conditions at the time of selection of an imaging mode or observation of image data or the like.

For example, as shown in FIG. 4, the mother preset condition storage unit stores in advance a mother preset condition MPa set for ultrasonic examination A and mother preset condition MPb set for ultrasonic examination B, and the sub-preset condition storage unit stores in advance a plurality of sub-preset conditions set by updating some of the mother preset conditions MPa and MPb for each imaging mode (the B mode, color Doppler mode, and spectrum Doppler mode) as a unit.

That is, the sub-preset condition storage unit stores B-mode sub-preset conditions Ba1 to Ba4, color Doppler mode sub-preset conditions Ca1 to Ca3, and spectrum Doppler sub-preset conditions Da1 to Da4 corresponding to the mother preset condition MPa, with the identification information of ultrasonic examination A or mother preset condition MPa serving as additional information, and also stores B-mode sub-preset conditions Bb1 to Bb5, color Doppler mode sub-preset conditions Cb1 to Cb3, and spectrum Doppler sub-preset conditions Db1 to Da4 corresponding to the mother preset condition MPb, with the identification information of ultrasonic examination B or mother preset condition MPb serving as additional information.

FIG. 5 shows a concrete example of the mother preset condition MPa corresponding to ultrasonic examination A which is stored in the mother preset condition storage unit of the preset condition storage unit 5. This mother preset condition storage unit stores, for example, "observation depth Dx", "ultrasonic wave focusing distance Fx", "scanning range Wx", "ultrasonic frequency fox", "reception gain Gx", and the like set in advance as B-mode mother preset conditions, "rate frequency frx", "filter frequency fcx", "ultrasonic frequency fox", "reception gain Gx", and the like set in advance as color Doppler mother preset conditions, and "rate frequency frx", "filter frequency fcx", "ultrasonic frequency fox", "reception gain Gx", "baseline shift frequency fs", and the like set in advance as spectrum mode mother preset conditions.

FIG. 6 shows a concrete example of the B-mode sub-preset conditions Ba1 to Ba4 corresponding to the mother preset condition MPa which are stored in the sub-preset condition storage unit of the preset condition storage unit 5. For example, the sub-preset condition Ba1 is formed by updating "observation depth Dx", "ultrasonic wave focusing distance Fx", and "scanning range Wx" of the mother preset condition MPa to "observation depth Da1", "ultrasonic wave focusing distance Fa1", and "scanning range Wa1", and the sub-preset condition Ba2 is formed by updating "observation depth Dx", "scanning range Wx", and "reception gain Gx" of the mother preset condition MPa to "observation depth Da2", "scanning range Wa2", and "reception gain Ga2". Likewise, the sub-preset condition Ba3 is formed by updating "observation depth Dx" and "scanning range Wx" of the mother preset condition MPa to "observation depth Da3" and "scanning range Wa3", and the sub-preset condition Ba4 is formed by updating "observation depth Dx" of the mother preset condition MPa to "observation depth Da4".

The sub-preset selection window generation unit 6 in FIG. 1 then receives examination selection information such as "ultrasonic examination A" and imaging mode selection information supplied from the system control unit 12, and extracts sub-preset conditions corresponding to these pieces of selection information from the respective types of sub-preset conditions stored in the sub-preset condition storage unit of the preset condition storage unit 5. The sub-preset selection window generation unit 6 then generates sub-preset selection window data in which one or a plurality of selection buttons indicating the names of obtained sub-preset conditions (sub-preset names) are arranged.

Obviously, sub-preset conditions which can be set are not limited to the example shown in FIG. 6. For example, first of all, selecting the sub-preset condition Ba1 shown in FIG. 7 will update "observation depth Dx", "ultrasonic wave focusing distance Fx", and "scanning range Wx" of the mother preset condition MPa to "observation depth Da1", "ultrasonic wave focusing distance Fa1", and "scanning range Wa1". Subsequently, selecting the sub-preset condition Ba2 constituted by the same combination of items can further update "observation depth Da1", "ultrasonic wave focusing distance Fa1", and "scanning range Wa1" to "observation depth Da2", "ultrasonic wave focusing distance Fa2", and "ultrasonic wave focusing distance Fa2", respectively.

In addition, as shown in FIG. 8, it is possible to set "probe type" as a sub-preset condition item. When acquiring a B-mode image of the lower extremity, the operator may scan the femoral area with a linear probe or scan the knee joint area with a convex probe. In such a case, first of all, upon scanning the femoral area with the linear probe, the operator changes the probe to be used from the linear probe to the convex probe, and selects a sub-preset condition Ba10. This makes it possible to quickly and easily change image data acquisition conditions to values suitable for the convex probe.

Note that even when the operator selects predetermined sub-preset conditions, and parameters are changed and updated, the currently activated imaging mode (B, Color, Doppler, or the like) is not changed but is maintained.

Figure 9A:
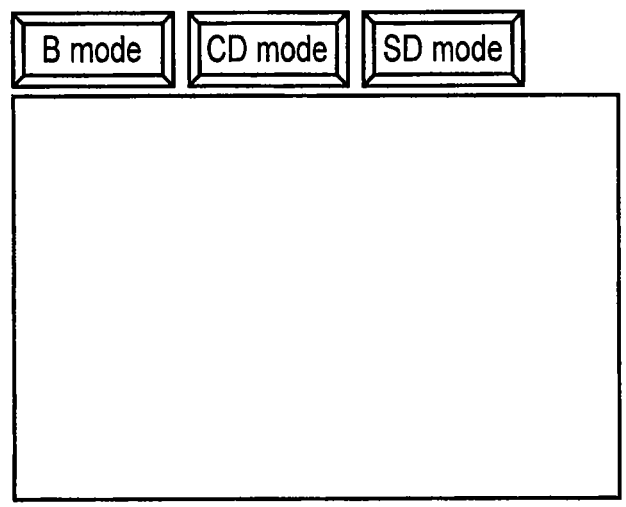
FIG. 9A is a view showing a concrete example of a sub-preset selection window in this embodiment.
Figure 9B:
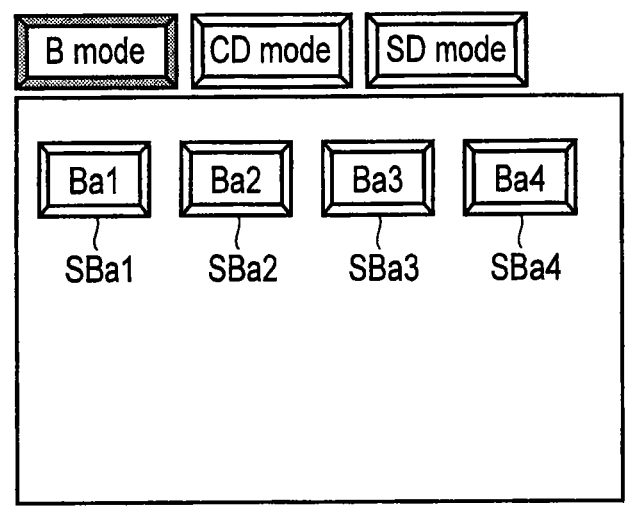
FIG. 9B is a view showing a concrete example of a sub-preset selection window in this embodiment.

FIGS. 9A, 9B, 9C, and 9D show concrete examples of the sub-preset selection window data generated by the sub-preset selection window generation unit 6. FIG. 9A shows the sub-preset selection window data when no imaging mode is selected. FIG. 9B shows the sub-preset selection window data when the B mode is selected. FIG. 9C shows the sub-preset selection window data when the color Doppler mode is selected. FIG. 9D shows the sub-preset selection window data when the spectrum Doppler mode is selected.

For example, if the B mode is selected as an imaging mode, the sub-preset selection window data shows selection buttons SBa1 to SBa4 respectively corresponding to the B-mode sub-preset conditions Ba1 to Ba4, as shown in FIG. 9B. If the color Doppler mode is selected, the sub-preset selection window data shows selection buttons SCa1 to SCa3 respectively corresponding to the color Doppler sub-preset conditions Ca1 to Ca3, as shown in FIG. 9C. Likewise, if the spectrum Doppler mode is selected, the sub-preset selection window data shows selection buttons SDa1 to SDa4 respectively corresponding to the spectrum Doppler mode sub-preset conditions SDa1 to SDa4, as shown in FIG. 9D.

Figure 10:
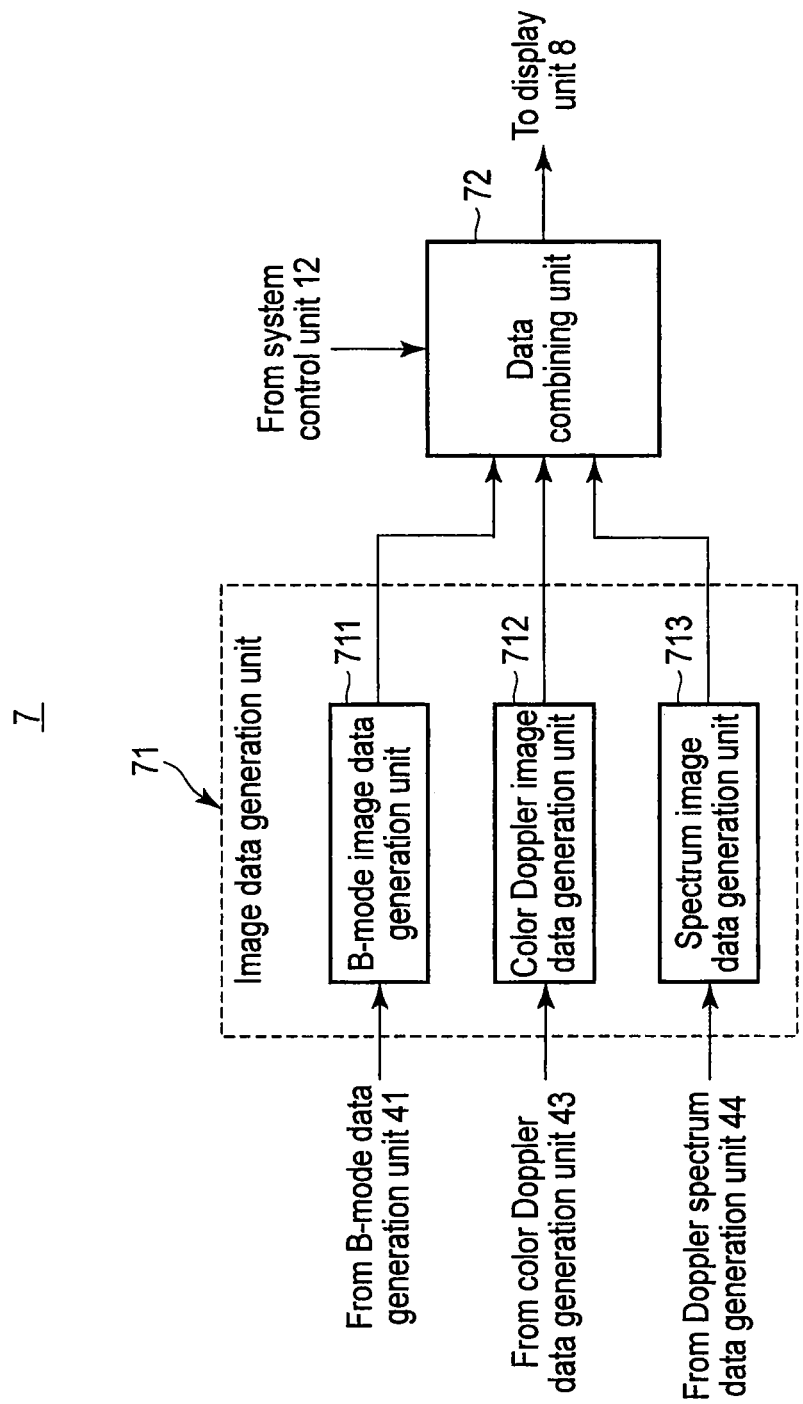
FIG. 10 is a block diagram showing the concrete arrangement of the display data generation unit of the ultrasonic diagnostic apparatus of this embodiment.

The concrete arrangement of the display data generation unit 7 shown in FIG. 1 will be described next with reference to FIG. 10. As shown in the block diagram of FIG. 10, the display data generation unit 7 includes an image data generation unit 71 which generates the respective types of image data based on the B-mode data, color Doppler data, and Doppler spectrum data generated by the reception signal processing unit 4, and a data combining unit 72 which generates display data by combining these image data and adding the object information, image data acquisition conditions, and the like supplied from the system control unit 12 to the resultant image data, as needed.

The image data generation unit 71 includes a B-mode image data generation unit 711, a color Doppler image data generation unit 712, and a spectrum image data generation unit 713. The B-mode image data generation unit 711 stores reception signals (B-mode data) after logarithmic conversion which are sequentially supplied from the B-mode data generation unit 41 of the reception signal processing unit 4 for each transmission/reception direction as a unit in the self storage circuit, and generates B-mode image data.

The color Doppler image data generation unit 712 generates color Doppler image data based on the color Doppler data supplied from the color Doppler data generation unit 43 of the reception signal processing unit 4. For example, the color Doppler image data generation unit 712 generates color Doppler image data which allows simultaneous observation of an average flow velocity value and a velocity variance by setting brightness information corresponding to the average blood flow velocity value and hue information corresponding to the velocity variance as pixel values, respectively.

The spectrum image data generation unit 713 generates spectrum image data by arranging, in the time axis direction, the time-series Doppler spectrum data generated by the Doppler spectrum data generation unit 44 of the reception signal processing unit 4 based on the Doppler signals obtained from a predetermined region of interest (range gate).

On the other hand, the data combining unit 72 generates display data by converting the B-mode image data, color Doppler image data, and spectrum image data supplied from the image data generation unit 71 into data in a predetermined display format and combining these image data having undergone the conversion processing.

The display unit 8 in FIG. 1 includes a conversion processing unit and monitor (not shown). The conversion processing unit performs conversion processing such as D/A conversion or television format conversion of the above display data supplied from the display data generation unit 7 and the sub-preset selection window data supplied from the sub-preset selection window generation unit 6, thereby displaying the resultant data on the monitor.

The input unit 9 includes input devices such as a display panel, keyboard, trackball, mouse, selection buttons, and slide levers on an operation panel, and has a function of selecting an imaging mode such as the B mode, color Doppler mode, or spectrum Doppler mode, a function of selecting sub-preset conditions, and a function of finely adjusting the image data acquisition conditions set/updated based on mother preset conditions and sub-preset conditions. In addition, the operator uses the above display panel and input devices to, for example, input object information, select ultrasonic examination, set display data generation conditions, and input various types of instruction signals including a sub-preset selection window display instruction signal.

The filter control unit 10 controls the filtering characteristics of the MTI filter 432 and HPF 442 by supplying the filter control signals generated based on the filter frequency and the like of the mother preset conditions or sub-preset conditions supplied from the preset condition storage unit 5 via the system control unit 12 to the MTI filter 432 of the color Doppler data generation unit 43 and the HPF 442 of the Doppler spectrum data generation unit 44. That is, supplying the above filter control signals will form the MTI filter 432 having a frequency characteristic suitable for the generation of color Doppler image data and the HPF 442 having a frequency characteristic suitable for the generation of spectrum image data.

The scanning control unit 11 performs delay time control on the transmission delay circuit 312 of the transmission unit 31 and the reception delay circuit 323 of the reception unit 32 for ultrasonic transmission/reception in the B mode, color Doppler mode, and spectrum Doppler mode set in advance for a two-dimensional region or three-dimensional region including a diagnostic target portion of the object based on the scanning range and ultrasonic focusing distance of the mother preset conditions or sub-preset conditions supplied from the preset condition storage unit 5 via the system control unit 12. Concrete examples of ultrasonic transmission/reception in the color Doppler mode and spectrum Doppler mode are described in Jpn. Pat. Appln. KOKAI Publication Nos. 2004-329609 and 2005-81081, and hence a detailed description of them will be omitted.

The system control unit 12 includes a CPU and storage circuit (not shown). The storage circuit stores the mother preset conditions and sub-preset conditions for the ultrasonic examination which are supplied from the preset condition storage unit 5 and various types of input information, selected information, and set information input/selected/set by the input unit 9. In this case, the system control unit 12 reads out the sub-preset conditions selected by the input unit 9 using the sub-preset selection window data displayed on the display unit 8 from the sub-preset condition storage unit of the preset condition storage unit 5, and stores them in the above storage circuit.

The CPU sets or updates image data acquisition conditions for the ultrasonic examination by using the mother preset conditions and sub-preset conditions read out from the above storage circuit, and comprehensively controls the respective units of the ultrasonic diagnostic apparatus 100 based on the image data acquisition conditions to execute the ultrasonic examination.

The system control unit 12 further includes an acquisition condition storage unit (not shown). This acquisition condition storage unit stores the image data acquisition conditions updated by sub-preset conditions or the image data acquisition conditions finely adjusted by input devices of the input unit 9, with the identification of the ultrasonic examination or imaging mode being additional information.

When the input unit 9 selects the same imaging mode a plurality of times, it is possible to efficiently acquire proper image data by generating image data for the imaging mode by using the image data acquisition conditions read out from the above acquisition condition storage unit.

(Image Data Acquisition Condition Setting/Updating Procedure)

An image data acquisition condition setting/updating procedure in this embodiment will be described along the flowchart of FIG. 11. The following will exemplify a case in which the apparatus acquires B-mode image data first, and then acquires color Doppler image data or spectrum image data. However, the order of acquisition of image data is not limited to the above order. Furthermore, the embodiment can be applied to a case in which the apparatus acquires one of the above types of image data.

Before ultrasonic examination on the object, the operator of the ultrasonic diagnostic apparatus 100 inputs object information and sets display data generation conditions with the input unit 9, and then inputs a set instruction signal for image data acquisition conditions. Upon receiving this instruction signal, the system control unit 12 initializes image data acquisition conditions for the respective types of imaging modes (i.e., the B mode, color Doppler mode, and spectrum Doppler mode) by supplying the mother preset conditions for the ultrasonic examination which are read out from the mother preset condition storage unit of the preset condition storage unit 5 to the related units of the ultrasonic diagnostic apparatus 100, together with the above display data generation conditions (step S1 in FIG. 11).

Upon completion of the above initialization, the operator inputs an image data generation start instruction signal with the input unit 9 (step S2 in FIG. 11), and further selects the B mode as an imaging mode (step S3 in FIG. 11).

Upon receiving the image data generation start instruction signal and the imaging mode selection information via the system control unit 12, the transmission/reception unit 3, the reception signal processing unit 4, and the display data generation unit 7 respectively select B-mode mother preset conditions from the mother preset conditions initialized as image data acquisition conditions, and display the B-mode image data generated based on the mother preset conditions on the monitor of the display unit 8 (step S4 in FIG. 11).

Upon observing the B-mode image data displayed on the display unit 8, the operator operates the input unit 9 to input a display instruction signal for a sub-preset selection window for the selection of sub-preset conditions (step S5 in FIG. 11).

Upon receiving the above display instruction signal via the system control unit 12, the sub-preset selection window generation unit 6 extracts sub-preset conditions corresponding to the above B-mode mother preset conditions from the respective types of sub-preset conditions stored in the sub-preset condition storage unit of the preset condition storage unit 5, generates B-mode sub-preset selection window data in which one or a plurality of selection buttons corresponding to the obtained sub-preset conditions are arranged, and displays the data on the display unit 8 (see FIG. 9B) (step S6 in FIG. 11).

The operator selects a selection button suitable for the ultrasonic examination from the various selection buttons (e.g., the selection buttons Ba1 to Ba4 in FIG. 9B) indicated on the B-mode sub-preset selection window displayed on the display unit 8. Upon receiving this selection information, the system control unit 12 selects B-mode sub-preset conditions corresponding to the selected selection buttons from the various types of preset conditions stored in the sub-preset condition storage unit of the preset condition storage unit 5 (step S7 in FIG. 11).

Supplying the obtained B-mode sub-preset conditions to the related units such as the transmission/reception unit 3 and the reception signal processing unit 4 will update the image data acquisition conditions for the ultrasonic examination which have already been set based on the mother preset conditions. The related units described above then generate B-mode image data based on the image data acquisition conditions updated by the B-mode sub-preset conditions, and display the obtained B-mode image data on the display unit 8 (step S8 in FIG. 11).

By observing the above image data displayed on the display unit 8, the operator determines whether the updated image data acquisition conditions are appropriate (step S9 in FIG. 11). If the conditions are inappropriate, the operator finely adjusts the inappropriate image data acquisition conditions by using the fine adjustment slide lever and the like provided for the input unit 9 (step S10 in FIG. 11).

Upon receiving the above finely adjusted information supplied from the input unit 9 via the system control unit 12, the related units such as the transmission/reception unit 3 and the reception signal processing unit 4 update the image data acquisition conditions, which have already been set based on the mother preset conditions and the B-mode sub-preset conditions, by using the above finely adjusted information, and displays the B-mode image data generated based on the image data acquisition conditions after the update on the display unit 8 (step S11 in FIG. 11).

When acquiring color Doppler image data or spectrum image data upon acquiring the above B-mode image data, the operator selects the color Doppler mode or the spectrum Doppler mode as an imaging mode with the input unit 9 (step S3 in FIG. 11). Upon receiving this selection information, the system control unit 12 controls the respective units of the ultrasonic diagnostic apparatus 100 to repeat steps S4 to S11 described above, thereby setting image data acquisition conditions suitable for each imaging mode and generating and displaying color Doppler image data or spectrum image data based on the image data acquisition conditions (steps S4 to S11 in FIG. 11).

According to the above embodiment, it is possible to acquire desired image data in a short period of time by updating the image data acquisition conditions, set in advance for each ultrasonic examination as a unit, based on the sub-preset conditions set in advance for each imaging mode as a unit, and generating image data based on the image data acquisition conditions after the update.

Selecting sub-preset conditions suitable for the ultrasonic examination from the various types of sub-preset conditions set in advance for each imaging mode as a unit, in particular, makes it easy to update the image data acquisition conditions initialized by the mother preset conditions. In addition, selecting desired sub-preset conditions from the above various types of sub-preset conditions indicated as selection buttons on the sub-preset selection window makes it easy to select sub-preset conditions.

In addition, finely adjusting the image data acquisition conditions updated by sub-preset conditions can accurately set image data acquisition conditions optimal for the ultrasonic examination.

When selecting the same imaging mode a plurality of times, it is possible to efficiently acquire suitable image data by temporarily storing the image data acquisition conditions updated by sub-preset conditions or the image data acquisition conditions finely adjusted by using the input devices of the input unit, and generating image data for the imaging mode by using the stored image data acquisition conditions.

Since image data acquisition conditions are updated for each imaging mode as a unit based on sub-preset conditions, it is possible to selectively update image data acquisition conditions in an imaging mode which requires updating. This can prevent unnecessary updating operation. It is therefore possible to greatly reduce the load on the operator as well as improving the examination efficiency with respect to the object.

Although the embodiment in this disclosure has been described above, the disclosure is not limited to the above embodiment and its modification and can be modified and executed. For example, although the above embodiment has exemplified the ultrasonic diagnostic apparatus 100 which can acquire B-mode image data, color Doppler image data, and spectrum image data, the embodiment may be an ultrasonic diagnostic apparatus which can acquire B-mode image and color Doppler image data or B-mode image data and spectrum image data or an ultrasonic diagnostic apparatus which can acquire any one of the following data: B-mode image data, color Doppler image, and spectrum image data.

Although the above description is about the ultrasonic diagnostic apparatus 100 which generates the above image data based on the reception signals obtained by sector scanning on an object, this embodiment may be an ultrasonic diagnostic apparatus which can perform other types of ultrasonic scanning such as convex scanning and linear scanning.

Although the above description has exemplified the case in which sub-preset selection window data and various types of image data are displayed on the same display unit, these data may be displayed on different display units. Note that sub-preset names indicated by the selection buttons of sub-preset selection window data may be decided based on an examination target organ name, operator name, object name, object age, body type, disease condition, and the like, or other user friendly names may be used. Adding such names to the above selection buttons makes it easier for an operator who does not have much clinical experience to select sub-preset conditions. FIG. 12 shows an example of selection button display of sub-preset selection window data in such a case. Note that "(6C3)" in FIG. 12 exemplifies the ID of a probe type.

Although the above embodiment has exemplified the case in which the image data acquisition conditions initialized by using mother preset conditions set in advance are updated by using the sub-preset conditions set in advance for each imaging mode as a unit, the image data acquisition conditions updated by using the above sub-preset conditions may be further updated by using other preset sub-preset conditions.

According to the above description, if the image data acquisition conditions updated by sub-preset conditions are inappropriate, the operator finely adjusts the image data acquisition conditions after the update by using input devices of the input unit 9. However, the operator may update image data acquisition conditions before update by using other sub-preset conditions set in advance for each imaging mode as a unit.

In addition, according to the above description, sub-preset conditions are selected under the observation of the image data generated based on the image data acquisition conditions initialized by using mother preset conditions. However, image data acquisition conditions may be initialized by using mother preset conditions and sub-preset conditions.

Furthermore, according to the above description, mother preset conditions and sub-preset conditions are set and image data acquisition conditions are set/updated based on these preset conditions for each ultrasonic examination as a unit. However, these operations may be performed for each object or operator as a unit.

Note that the respective units included in the ultrasonic diagnostic apparatus 100 of this embodiment can be implemented by, for example, using a computer constituted by a CPU, RAM, magnetic storage device, input device, display device, and the like as hardware. For example, the system control unit 12 of the ultrasonic diagnostic apparatus 100 can implement various functions by causing the processor such as the CUP mounted in the above computer to execute predetermined control programs. In this case, the above control programs may be installed in the computer in advance or stored in a computer-readable storage medium. Alternatively, control programs distributed via a network may be installed in the computer.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus, comprising:
a preset condition memory
storing a plurality of mother preset condition sets, each mother preset condition set including, for a first imaging mode and a second imaging mode, first image data acquisition conditions corresponding to first image data acquisition items, and
storing at least one sub-preset condition set for each mother preset condition set, each sub-preset condition set including, for the first imaging mode and the second imaging mode, second image data acquisition conditions corresponding to second image data acquisition items,
wherein each of the first image data acquisition items and the second image data acquisition items includes a third image data acquisition item for the first imaging mode, and
one of the first image data acquisition conditions corresponding to the third image data acquisition item and one of the second image data acquisition conditions corresponding to the third image data acquisition item are different; and
processing circuitry configured to
select one of the mother preset condition sets and the first imaging mode,
initialize at least one of the first image data acquisition conditions corresponding to at least one of the image data acquisition items for the first imaging mode, wherein the at least one of the first image data acquisition conditions is included in the selected mother preset condition set and includes the one of the first image data acquisition conditions corresponding to the third image data acquisition item,
generate first image data based on first reception signals obtained by ultrasonic transmissions and receptions using the initialized at least one of the first image data acquisition conditions,
select one of the at least one sub-preset condition set associated with the selected mother preset condition set and corresponding to the first imaging mode,
update the one of the first image data acquisition conditions corresponding to the third image data acquisition item using the one of the second image data acquisition conditions corresponding to the third image data acquisition item and included in the one of the at least one sub-preset condition set, and
generate second image data based on second reception signals obtained by ultrasonic transmissions and receptions using the one of the second image data acquisition conditions corresponding to the third image data acquisition item and included in the one of the at least one sub-preset condition set.

2. The ultrasonic diagnostic apparatus of claim 1, wherein the preset condition memory further stores the plurality of mother preset condition sets, which are obtained by classifying image data acquisition conditions for each ultrasonic examination, as a group.

3. The ultrasonic diagnostic apparatus of claim 1, wherein the preset condition memory further stores the each sub-preset condition set, which is obtained by classifying image data acquisition conditions included in each mother preset condition set for each imaging mode, as a group.

4. The ultrasonic diagnostic apparatus of claim 3, wherein the preset condition memory further stores the each sub-preset condition set by updating an image data acquisition condition included in the corresponding mother preset condition set with reference to at least one of a body type, age, disease name, and disease condition of an object and a type of ultrasonic probe used for the ultrasonic transmission/reception.

5. The ultrasonic diagnostic apparatus of claim 3, wherein the processing circuitry is further configured to select one of the at least one sub-preset condition set, which is suitable for ultrasonic examination on the object, based on an updated imaging mode.

6. The ultrasonic diagnostic apparatus of claim 1, wherein the processing circuitry is further configured to
control display of the at least one sub-preset condition set corresponding to the selected mother preset condition set, and
select the one of the at least one sub-preset condition set, which is suitable for ultrasonic examination on the object, in response to operation via the display.

7. The ultrasonic diagnostic apparatus of claim 6, wherein the processing circuitry is further configured to control display of the at least one sub-preset condition set as at least one selection button classified for each imaging mode as a group.

8. The ultrasonic diagnostic apparatus of claim 6, wherein the processing circuitry is further configured to control display of the at least one sub-preset condition set as at least one selection button classified with reference to at least one of a body type, a disease name, a disease condition, a name of an object, an operator name, and an examination target organ name.

9. The ultrasonic diagnostic apparatus of claim 6, wherein the processing circuitry is further configured to further update the at least one of the image data acquisition conditions updated by the selected sub-preset condition set by using another sub-preset condition set selected via the display.

10. The ultrasonic diagnostic apparatus of claim 1, wherein the processing circuitry is further configured to
input a condition or a value for adjusting the at least one of the image data acquisition conditions updated by using the selected sub-preset condition set,
adjust the at least one of the image data acquisition conditions updated by using the selected sub-preset condition set based on the condition or the input value, and
generate image data based on a reception signal in ultrasonic transmission/reception by using the at least one of the image data acquisition conditions after adjustment.

11. An ultrasonic diagnostic apparatus control method for an ultrasonic diagnostic apparatus, comprising:
storing a plurality of mother preset condition sets, each mother preset condition set including, for a first imaging mode and a second imaging mode, first image data acquisition conditions corresponding to first image data acquisition items,
storing at least one sub-preset condition set for each mother preset condition set, each sub-preset condition set including, for the first imaging mode and the second imaging mode, second image data acquisition conditions corresponding to second image data acquisition items wherein each of the first image data acquisition items and the second image data acquisition items includes a third image data acquisition item for the first imaging mode, and one of the first image data acquisition conditions corresponding to the third image data acquisition item and one of the second image data acquisition conditions corresponding to the third image data acquisition item are different; and selecting one of the mother preset condition sets and the first imaging mode, initializing at least one of the first image data acquisition conditions corresponding to at least one of the image data acquisition items for the first imaging mode, wherein the at least one of the first image data acquisition conditions is included in the selected mother preset condition set and includes the one of the first image data acquisition conditions corresponding to the third image data acquisition item, generating first image data based on first reception signals obtained by ultrasonic transmissions and receptions using the initialized at least one of the first image data acquisition conditions, selecting one of the at least one sub-preset condition set associated with the selected mother preset condition set and corresponding to the first imaging mode, updating the one of the first image data acquisition conditions corresponding to the third image data acquisition item using the one of the second image data acquisition conditions corresponding to the third image data acquisition item and included in the one of the at least one sub-preset condition set, and generating second image data based on second reception signals obtained by ultrasonic transmissions and receptions using the one of the second image data acquisition conditions corresponding to the third image data acquisition item and included in the one of the at least one sub-preset condition set.

12. The ultrasonic diagnostic apparatus control method of claim 11, wherein the plurality of mother preset condition sets are obtained by classifying image data acquisition conditions for each ultrasonic examination as a group.

13. The ultrasonic diagnostic apparatus control method of claim 11, wherein the each sub-preset condition set is obtained by classifying image data acquisition conditions included in each mother preset condition set for each imaging mode as a group.

14. The ultrasonic diagnostic apparatus control method of claim 13, wherein the each sub-preset condition set is set by updating an image data acquisition item included in the corresponding mother preset condition set with reference to at least one of a body type, age, disease name, and disease condition of an object and a type of ultrasonic probe used for the ultrasonic transmission/reception.

15. The ultrasonic diagnostic apparatus control method of claim 13, wherein the setting of the sub-preset condition set comprises selecting the one of the at least one sub-preset condition set, which is suitable for ultrasonic examination on the object, based on an updated imaging mode.

16. The ultrasonic diagnostic apparatus control method of claim 11, further comprising displaying the at least one sub-preset condition set corresponding to the selected mother preset condition set, wherein the selecting of the one of the at least one sub-preset condition set comprises selecting one of the at least one sub-preset condition set, which is suitable for ultrasonic examination on the object, in response to operation via a display.

17. The ultrasonic diagnostic apparatus control method of claim 16, wherein the displaying comprises displaying the at least one sub-preset condition set as at least one selection button classified for each imaging mode as a group.

18. The ultrasonic diagnostic apparatus control method of claim 16, wherein the displaying comprises displaying the at least one sub-preset condition set as at least one selection button classified with reference to at least one of a body type, a disease name, a disease condition, a name of an object, an operator name, and an examination target organ name.

19. The ultrasonic diagnostic apparatus control method of claim 16, further comprising updating the at least one of the image data acquisition conditions updated by the selected sub-preset condition set by using another sub-preset condition set selected via the display.

20. The ultrasonic diagnostic apparatus control method of claim 11, further comprising:

inputting a condition or a value for adjusting the at least one of the image data acquisition conditions updated by using the selected sub-preset condition set, adjusting the at least one of the image data acquisition conditions updated by using the selected sub-preset condition set based on the condition or the input value; and generating image data based on a reception signal in ultrasonic transmission/reception by using the at least one of the image data acquisition conditions after adjustment.

21. A medical image diagnostic apparatus which acquires data by imaging an object and generates image data, comprising:

a preset condition memory storing a plurality of mother preset condition sets, each mother preset condition set including, for a first imaging mode and a second imaging mode, first image data acquisition conditions corresponding to first image data acquisition items, and storing at least one sub-preset condition set for each mother preset condition set, each sub-preset condition set including, for the first imaging mode and the second imaging mode, second image data acquisition conditions corresponding to second image data acquisition items, wherein each of the first image data acquisition items and the second image data acquisition items includes a third image data acquisition item for the first imaging mode, and one of the first image data acquisition conditions corresponding to the third image data acquisition item and one of the second image data acquisition conditions corresponding to the third image data acquisition item are different; and processing circuitry configured to select one of the mother preset condition sets and the first imaging mode, initialize at least one of the first image data acquisition conditions corresponding to at least one of the image data acquisition items for the first imaging mode, wherein the at least one of the first image data acquisition conditions is included in the selected mother preset condition set and includes the one of the first image data acquisition conditions corresponding to the third image data acquisition item, generate first image data based on first reception signals obtained by ultrasonic transmissions and receptions using the initialized at least one of the first image data acquisition conditions, select one of the at least one sub-preset condition set associated with the selected mother preset condition set and corresponding to the first imaging mode, update the one of the first image data acquisition conditions corresponding to the third image data acquisition item using the one of the second image data acquisition conditions corresponding to the third image data acquisition item and included in the one of the at least one sub-preset condition set, and generate second image data based on second reception signals obtained by ultrasonic transmissions and receptions using the one of the second image data acquisition conditions corresponding to the third image data acquisition item and included in the one of the at least one sub-preset condition set.

22. The apparatus of claim 1, wherein the processing circuitry is further configured to control ultrasound transmissions and receptions using at least one of the first image data acquisition conditions corresponding at least one of the first image data acquisition items for the second imaging mode when the second imaging mode is selected while the mother preset is selected, and control ultrasound transmissions and receptions using at least one of the second image data acquisition conditions corresponding at least one of the second image data acquisition items for the second imaging mode when the second imaging mode is selected while the one of the at least one sub-preset condition set is selected.

23. The apparatus of claim 1, wherein the first imaging mode is a B-mode.

24. The apparatus of claim 23, wherein the second imaging mode is a color Doppler mode.

25. The apparatus of claim 23, wherein the second imaging mode is a spectrum Doppler mode.

26. The apparatus of claim 1, wherein the processing circuitry configured to select the one of the at least one sub-preset condition set associated with the selected mother preset condition set and corresponding to the first imaging mode is configured to select the one of the at least one sub-preset condition set associated with the selected mother preset condition set and corresponding to the first imaging mode using a sub-preset selection window.

* * * * *